Figure 1:
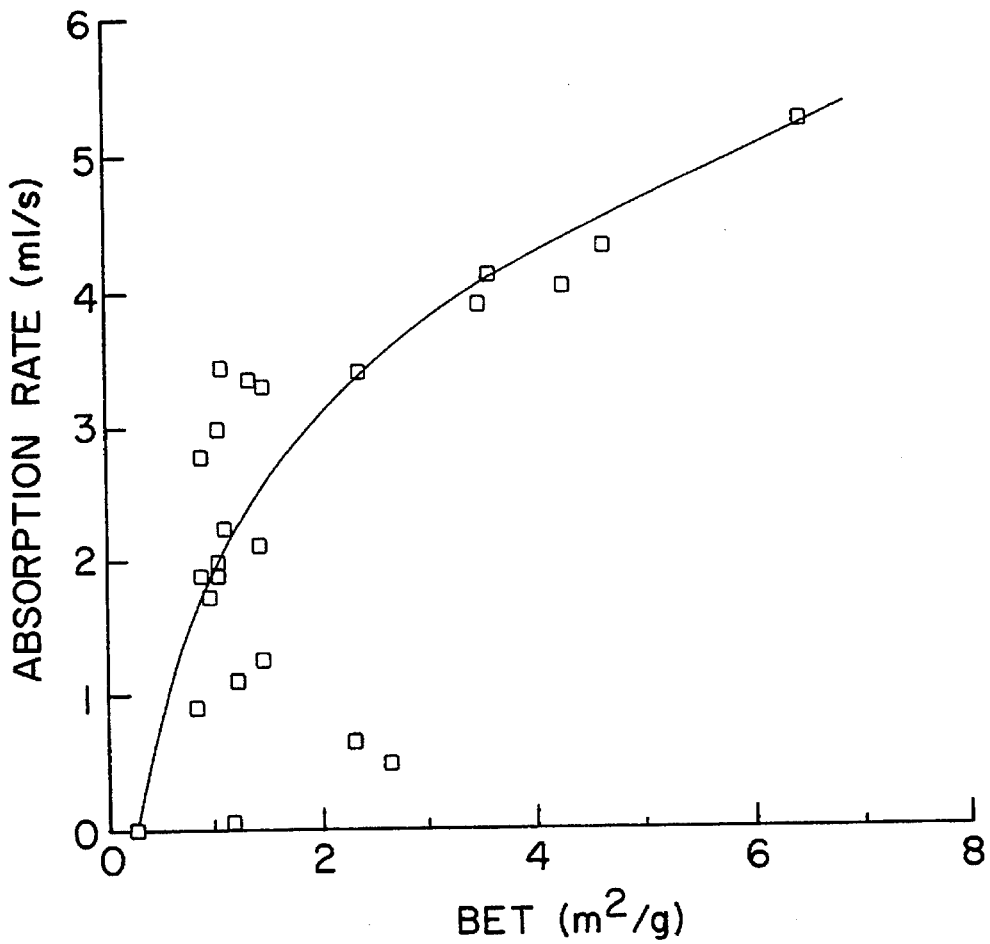

United States Patent [19]

Eriksson et al.

[11] Patent Number: 5,492,759
[45] Date of Patent: Feb. 20, 1996

[54] FIBRES OF INCREASED SPECIFIC SURFACE AREA, A METHOD FOR THEIR MANUFACTURE, FLUFF PULP CONSISTING OF SUCH FIBRES AND THE USE OF THE FIBRES AS ABSORPTION MATERIAL

[75] Inventors: Inger V. Eriksson; Göran E. Annergren; Lars E. R. Wågberg, all of Sundsvall, Sweden

[73] Assignee: Molnlycke AB, Goteborg, Sweden

[21] Appl. No.: 842,381

[22] PCT Filed: Sep. 27, 1990

[86] PCT No.: PCT/SE90/00622

§ 371 Date: May 5, 1992

§ 102(e) Date: May 5, 1992

[87] PCT Pub. No.: WO91/05108

PCT Pub. Date: Apr. 18, 1991

[30] Foreign Application Priority Data

Sep. 27, 1989 [SE] Sweden ................................ 8903180
Jul. 20, 1990 [SE] Sweden ................................ 9002476

[51] Int. Cl.$^6$ ............................................ D02G 3/00
[52] U.S. Cl. ........................ 428/375; 428/357; 428/373; 428/379; 428/342; 536/56; 604/350; 604/360; 604/375; 604/904
[58] Field of Search .................... 428/357, 364, 428/375, 361, 373, 374, 379, 342; 162/157, 146, 157.1; 8/116.1, 116.2, 116.4; 167/84, 90; 260/438; 536/56; 604/904, 350, 360, 375

[56] References Cited

U.S. PATENT DOCUMENTS

| | | | |
|---|---|---|---|
| 2,762,822 | 3/1954 | Vagemius | 260/438 |
| 2,856,330 | 10/1958 | Vagemius | 167/84 |
| 3,172,817 | 3/1965 | Leupold et al. | 167/90 |
| 3,932,209 | 1/1976 | Chatterjee | 162/157 |
| 4,385,632 | 5/1983 | Odelhog | 604/360 |
| 5,104,411 | 4/1992 | Makoui et al. | 8/116.4 |

FOREIGN PATENT DOCUMENTS

| | | |
|---|---|---|
| 0080382 | 6/1983 | European Pat. Off. . |
| 101319 | 4/1987 | European Pat. Off. . |
| 252650 | 2/1988 | European Pat. Off. . |
| 276200 | 7/1988 | European Pat. Off. . |
| 0276200 | 7/1988 | European Pat. Off. . |
| 0304952 | 3/1989 | European Pat. Off. . |
| 304952 | 3/1989 | European Pat. Off. . |
| 1424692 | 2/1976 | United Kingdom . |
| WO88/06659 | 9/1977 | WIPO . |

Primary Examiner—Patrick J. Ryan
Assistant Examiner—Merrill Dixon
Attorney, Agent, or Firm—Young & Thompson

[57] ABSTRACT

Fibres which have an increased specific surface area and improved absorption properties, preferably intended for use in the form of fluff pulp in absorption articles such as diapers, incontinence guards, etc., in which the fibres present a porous layer of hydrophilic chemicals anchored on the fibre surface; a method of producing such fibres, their use in absorption articles and an absorption material which includes the fibres.

25 Claims, 1 Drawing Sheet

FIBRES OF INCREASED SPECIFIC SURFACE AREA, A METHOD FOR THEIR MANUFACTURE, FLUFF PULP CONSISTING OF SUCH FIBRES AND THE USE OF THE FIBRES AS ABSORPTION MATERIAL

The present invention relates to the field of absorption material, and particularly to absorption material for use in the manufacture of sanitary articles such as diapers, incontinence guards, drying cloths and the like, the absorbent material of such articles containing fibres of enlarged specific surface area and therewith a high absorption rate. The invention also relates to a method of manufacturing these fibres, their use in the form of fluff pulp or in mixture with untreated fibres in the form of fluff pulp, in order to obtain improved absorption.

One generally known problem within the field of the manufacture of absorbent material for use, preferably in the production of sanitary articles, such as diapers, incontinence guards, etc., resides in the achievement of optimum absorption rates and dispersion or distribution properties with respect to the absorption and dispersion of liquid in the fibre material of the fluff pulp.

Our earlier filed Swedish Patent Application No. 8903180-1. from which convention priority is requested for the present Patent Application, describes a method of treating cellulose fibres intended for absorption purposes, wherein the absorption properties of a cellulose-based fibre material are improved by precipitating silicate onto the fibre walls in situ, this precipitation being effected in a two-stage process. In the first of these stages, the fibres are impregnated with an alkali silicate and, after being dewatered, the fibres are treated with an aluminium salt solution, subsequent to adjusting the pH to a value of at most 9. This treatment results in the precipitation of silicate onto the fibre walls, which improves liquid transportation and liquid retention, and also prevents swelling collapse when drying.

Our Swedish Patent Application 9002475-3 (our reference No. 20677) filed simultaneously with the present application describes fibres treated with an aluminium salt solution, these fibres also resulting in a material of increased absorption rate without the addition of silicate, even though the presence of silicate affords some further improvement. The treatment is carried out at given pH-ranges, namely at pH=5–11, preferably pH= 8.5– 9.5, particulary at pH= 9.

Thus, when applying the present invention there is obtained an increase in the specific surface area of the fibres, intended in particular as absorbent material in sanitary articles, this enlarged specific surface area resulting in a markedly improved absorption rate and liquid transport of the fibre material. Subsequent to being treated with hydrophilic chemicals, the fibre surface exhibits a relatively thin porous layer, i.e. a layer having a thickness less than 2000 Å.

The porous layer is obtained by treating (impregnating) the fibre material with hydrophilic chemicals, the fibres being in either a dry state or a moist state, either in the form of a dewatered fibre pulp or in the form of a fibre-water suspension. This treatment process may be effected by bringing the fibres, in one of the aforesaid states, into contact with the hydrophilic chemicals, e.g. by spraying the fibres in a dry or moist state. with a chemical solution, or by mixing the chemicals with a fibre dispersion, where the chemicals are supplied in a solid, commercially available state or in the form of a solution. This admixture or spraying process can be carried out with the aid of typical equipment used conventionally in this technique.

Other appropriate treatment conditions are conventional, and optimum conditions can be readily established by the person skilled in this art, e.g. conditions concerning pH, temperature, mixing speed, chemical quantities, impregnation times, etc.

The interaction between fibres and precipitation chemicals can be achieved in a number of ways. Van der Waals interaction and/or electrostatic interaction (including, inter alia, adsorption of precipitation chemicals on the fibre surface) exist between fibres and precipitation chemicals. Furthermore, flocculation/precipitation takes place alone or in combination with the aforedescribed interaction phenomenon. This flocculation/precipitation product is anchored to the fibre surface much as a result of the surface irregularities present.

The hydrophilic chemicals used can also be seen as "precipitation chemicals", i.e. the porous layer is formed by a "precipitation" or "flocculation" of the chemicals which when anchored on the fibre surface by one of the aforesaid mechanisms therewith providing the surface enlargement which results in the desired improvement of the absorption properties.

Thus, by "chemical bonding" is meant an electrostatic bond between the fibre and the positive cation in the precipitation chemical, or alternatively van der Waals forces. For the purpose of obtaining a "surface coating", the chemical is sprayed onto the fibres and there anchored by drying. By the term "precipitation" is meant that a soluble substance converts to a solid state as a result of a change in the concentration of the solution such as to exceed the solubility product. By flocculation is meant in this case an agglomeration of so-called microparticles to larger agglomerates which, however, are still colloidally stable. An additional destabilization can take place in this process, where said flocculated micro particles are further destabilized and therewith precipitated in a non-colloidal stable state. In the present case, this latter process is designated coagulation. These latter precipitates are assumed to have a denser structure.

In the present case, the term precipitation chemicals is considered to be the most relevant term for the chemicals used to bond the hydrophilic complex to the fibre surface and therewith produce the aforesaid porous layer. It should be noted, however, that the precipitation chemical may form part of the hydrophilic precipitate.

The precise mechanism of the anchoring mechanisms involved in the present invention have not been fully established and are thought to be insignificant to the effect achieved by the invention. Obviously, a number of different chemical processes and physical processes take place.

For instance, the surface coating can be produced by precipitation and subsequent coagulation of the precipitation chemical supplied on the fibre surfaces, therewith forming a porous layer on said surfaces. Thus, in this case, two mechanisms are involved, firstly precipitation with subsequent particle agglomeration and secondly chemical bonding of the chemical with the fibre surface. The sequence in which these processes take place has not been established.

Bonding takes place on the electronegative groups on the fibre surface, e.g. hydroxyl, carboxyl and sulfonic acid groups. Such groups are found, for instance, on lignin, cellulose, hemicellulose and extractive substances.

A concrete example of an anchoring situation may, for instance, involve the bonding of iron ions or aluminium ions to the carboxyl group, —COOH, on hemicellulose for instance. It is well known that this process may create a positive patch on the fibre surface which in turn then may bind an anionic precipitate. It is probable that this is the process which takes place at low pH values.

The fibre suspension normally contains a number of different substances originating partly from the starting material used in the production of the fibres and partly from additive materials, e.g. colloidal materials having particle sizes in the order of 0.01–5 μm ($10^{-6}$ m), such as fatty acids, resin acid, sulphonates, various kinds of hemicellulose, lignin fragments, water glass, inorganic salts (e.g. Ca and Mg from the process water) and small fibres, so-called fines.

A very common explanation to the observed reactions is simply in ion/ion interaction between oppositely charged species. One reason for the high effectiveness of multivalent cations is the effect described via the so-called Schulze-Hardy's rule, i.e. the effectiveness of the cation, from the aspect of coagulation, increases with (ion valence)$^2$ or (the ion valence)$^6$. Furthermore the precipitation chemical can cross-link two fibres with elecrostatic bonds. This precipitation has also fundamentally been described in the literature (Buttero, J.Y. et al, Langmuir 1990, 6, 596–602).

The flocculation of the dissolved and colloidal material is thus dependent on pH and on the ion concentration, and is specific for every specific precipitation chemical. In the process of flocculation, a voluminous floc is probably formed which, by charge neutralization or bridging between different colloids aggregates the colloids present in the pulp suspension and in this way includes these colloids in the formed floc. Chemical precipitation of a compound takes place when the product of the molar concentrations of the ions present in the compound exceed the solubility product.

The complex formed is thus a metal hydroxide complex and also a metal oxide complex. According to the above mentioned mechanism, a co-precipitation can also take place, where "foreign" substances become incorporated.

In a concrete case, where aluminium chloride is used as the precipitation chemical and the fibre suspension contains cellulose fibres whose absorption properties it is desired to improve, the mechanism by which the porous layer is precipitated and anchored can be explained by the following model:

Two exchange mechanisms can take place between aluminium chloride and cellulose fibres, firstly an ion-exchange of aluminium ions with cations associated with the carboxyl group on the fibre, and secondly the formation of aluminium flocs. The mutual size or magnitude of these two mechanisms depends, among other things, on the degree of neutralization of the aluminium chloride. The exchange between aluminium ions and hydroxyl ions results in the formation of electrically charged hydroxyl aluminium polymers. The high electrical charge of these complex aluminium compounds layouts the coagulation of negative particles.

Polyaluminium ions would seem to function more effectively than normal aluminium ions. The explanation to this may possibly be their high ion charge, which according to the earlier mentioned Schulze-Hardy's rule causes counter ions of high valency (so-called CCC-values) to result in very low critical coagulation concentrations. Since the charge is very high for polyaluminium solutions, this would explain the superior properties of such solutions in comparision with typical aluminium ions. The aluminium silicate complex is negatively charged at basic pH-values and thus binds different cations as counter ions.

Anchoring of the porous layer can also be improved by adding native, e.g. cationic starch derivatives, cationic galactomannan derivatives and/or synthetic polymers.

By synthetic polymers the following chemicals may be considered:

A) Chain reaction polymers are produced from monomers of the ethyl acrylates type having quaternary ammonium salts as terminal groups.

B) Modified polyacrylamides where the polyacrylamide is reacted with HCHO and dimethylamine.

C) Polydiallyl dialkyl-ammonium halogenides.

D) Cationic amide amines.

E) Condensation products between dicyano diamide, formaldehyde and an ammonium salt.

F) Reaction products between epichlorohydrin or poly-epichlorohydrin and ammonia, amines.

G) Polymers formed by reaction between amines and dihalo alkanes.

H) Polymers formed by polymerization of ethylenimine.

I) Polymers formed by polymerization of N-(dialkyl-amino alkyl)-acryl-amide-monomers.

J) Natural polymers as specified in "Industrial Gums", R. L. Whistler, Academic Press. New York, London 1959.

It is essential that the bond effected between the porous, hydrophilic layer and the fibre surface is sufficiently strong to withstand all further conceivable forms of treatment to which the fibres may be subjected, for instance defibration of the pulp, air transport and other processes applied in conjunction with the conversion.

The porous layer anchored on the fibre surface consists mainly of precipitation chemicals, although the layer may also include, for instance, a co-precipitate of colloids from surrounding aqueous environments. The precipitation chemicals consist of hydrophilic positive inorganic ions, which are supplied, for instance, in the form of salts, hydroxides or oxides, and which bond, for instance, to the hydroxyl, carboxyl and/or sulphonic acid groups present on the fibre surface. The positive inorganic ions are preferably alkali metals and alkaline earth metals and $Al^{3+}$, $Fe^{3+}$, $Mg^{2+}$, $Fe^{2+}$, $Mn^{2+}$ or $Cu^{2+}$. The Porous layer may also include mixtures of these ions. Sulphate, chloride, carbonate, phosphate and/or hydroxide are preferably used as negative ions in the salts of these inorganic ions.

According to one preferred embodiment, the alkali metal ions are supplied in the form of sodiummetasilicate and the alkaline earth metal are supplied in the form of calcium sulphate, calcium carbonate or calcium chloride, optionally in the presence of carbon dioxide. Lime, $Ca(OH)_2$ or $CaO$ will also function as a surface enlarging chemical, when precipitated on the surfaces of the fibres.

Aluminium ions are preferably supplied in the form of poly(aluminium chloride) or poly(aluminium sulphate). aluminium phosphate or sodium aluminate. Mixtures of these compounds can also be used. The iron ions are also preferably supplied in polymer form, for instance poly(iron sulphate) or poly(iron chloride).

The resultant surface enlarging effect is amplified and subsequent improvement of the absorption properties is obtained when anchoring is effected in the presence of silicate, either with the addition of silicate in a separate impregnating stage or with the aid of silicate already present in, e.g., an aqueous solution of cellulose fibres residual from the bleaching stage.

The fibres themselves may have different origins, and may comprise cellulosic fibres, e.g. chemimechanical (CTMP) or chemical pulp fibres, or rayon fibres. The fibres may also consist of synthetic fibres, for instance polypropylene, polyester and polyvinyl alcohol fibres. The fibres may also have a natural origin, e.g. originate from grass, white moss or peat. Mixtures of fibres may also be used, both in the fibre suspension subjected to the surface enlarging treatment, and in fluff pulp intended for absorbent purposes, partly as a fibre mixture in the actual absorbent body itself and partly in different layers which form the absorbent body. Furthermore, the treated fibres may be mixed with non-treated fibres or layers thereof, wherewith so-called superabsorbents may also be included in the absorption material.

IN THE DRAWINGS

Figure 2:
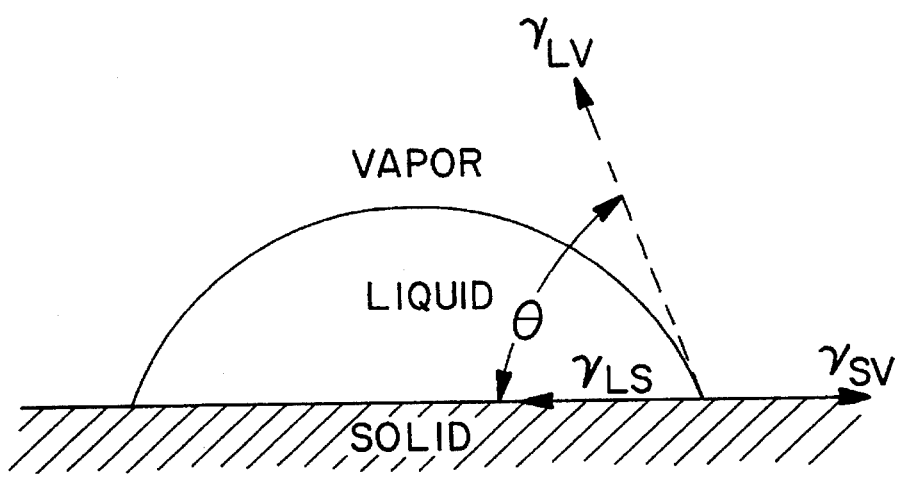

FIG. 1 is a graph showing the relationship between specific surface area and absorption rate, and FIG. 2 is a diagram illustrating the way in which contact angle is conventionally measured.

The porous layer anchored to the fibre surface by means of the above processes thus provides an improved absorption rate due to the increased specific surface area of the fibre. Given below is a table which shows the relationship between specific surface area and absorption rate, this relationship also being shown in the accompanying FIG. 1.

TABLE I

Relationship Between Specific Surface Area and Absorption Rate

| Sample | Specific Surface Area m²/g | Absorption Rate ml/s |
|---|---|---|
| 1 | 3.580 | 4.100 |
| 2 | 1.210 | 1.100 |
| 3 | 4.280 | 4.020 |
| 4 | 1.170 | 0.060 |
| 5 | 1.040 | 1.880 |
| 6 | 1.350 | 3.350 |
| 7 | 1.040 | 1.980 |
| 8 | 0.0810 | 0.890 |
| 9 | 6.440 | 5.220 |
| 10 | 1.070 | 3.430 |
| 11 | 1.030 | 2.990 |
| 12 | 0.860 | 2.770 |
| 13 | 1.030 | 1.840 |
| 14 | 1.460 | 1.230 |
| 15 | 0.970 | 1.700 |
| 16 | 2.390 | 3.400 |
| 17 | 1.430 | 2.100 |
| 18 | 1.470 | 3.280 |
| 19 | 3.510 | 3.880 |
| 20 | 4.650 | 4.320 |
| 21 | 0.870 | 1.880 |
| 22 | 1.080 | 2.240 |
| 23 | 0.249 | 0.01 |
| 24 | 2.307 | 0.650 |
| 25 | 2.644 | 0.510 |

N.B.:
The specific surface area is measured in accordance with the BET-method and the absorption rate is measured in accordance with "The Porous Plate Testing Apparatus" (Textile Res. J., pages 356-366, 1967, Burgeni and Kapur: "Capillary Sorption Equilibria in Fiber Masses").

Thus, subsequent to applying the porous layer the specific surface area of a treated fibre will have the values of at least 1.2 m²/g, especially at least 1.6 m²/g and preferably at least 2.1 m²/g in order to achieve the desired improvement in absorption properties. The specific surface area is measured in accordance with the BET-method, and the value of non-treated cellulose fibres for instance is about 1 m²/g, whereas the value of such fibres after treatment is 3–7 m²/g.

It is also found that the contact angle of the porous layer, measured on compressed sheets of the fibre material, is also a factor which exhibits correlation with the absorption rate. Thus, the contact angle should be at most 70°, particularly at most 65° and preferably at most 60°. The following table illustrates the relationship between absorption rate and contact angle (see Table II and FIG. 2).

In FIG. 2, the contact angle is $\theta$; $\gamma_{LS}$ is the zero angle of the liquid-solid interface; $\gamma_{LV}$ is the tangent to the liquid-vapor interface at the liquid-solid interface; and $\gamma_{SV}$ is the solid-vapor interface angle.

TABLE II

Relationship Between Absorption Rate and Contact Angle

| Absorption Rate (ml/s) | Contact Angle (°) |
|---|---|
| 0.29 | 65.5 |
| 0.42 | 63.8 |
| 0.71 | 68.5 |
| 0.25 | 72.5 |
| 1.29 | 65.0 |
| 2.08 | 42.6 |
| 2.09 | 60.6 |
| 3.04 | 55.8 |
| 1.52 | 50.7 |
| 1.59 | 60.5 |

The layer anchored to the fibre surface shall be porous, the porosity being defined as the air volume distribution in the porous material. The porosity is determined by the ratio of air volume to total bulk volume of the material and thus lies between 0 and 1. The porosity is dimensionless. Other magnitudes which are relevant to porous material are, for instance, pore volume, pore diameter and pore area. The porous layer formed on the fibres in accordance with this invention exhibits a high percentage of pores of small diameter, which thus provides a large specific surface area when seen in total. The majority of the pores have a diameter smaller than 500 Å, particularly smaller than 300 Å and perferably smaller than 200 Å.

A series of measurements of pore diameter, pore volume and pore area respectively have been carried out on the aluminium complex preferably used in accordance with the present invention. The results obtained are shown in the following Table III.

TABLE III

Relationship Between Pore Diameter, Pore Volume and Pore Area

| Pore Diameter Å | Pore Volume (mm³/g) | Pore Area (m²/g) |
|---|---|---|
| 2650-1840 | 0.092 | 0.002 |
| 1840-1703 | 0.228 | 0.005 |
| 1703-1482 | 0.336 | 0.009 |
| 1482-1213 | 0.328 | 0.010 |
| 1213-931 | 0.779 | 0.030 |
| 931-737 | 0.680 | 0.034 |
| 838-576 | 0.581 | 0.037 |
| 576-497 | 0.411 | 0.031 |
| 497-450 | 0.259 | 0.022 |
| 450-406 | 0.285 | 0.027 |
| 406-341 | 0.427 | 0.047 |
| 341-293 | 0.347 | 0.044 |
| 293-256 | 0.313 | 0.046 |
| 256-228 | 0.319 | 0.053 |
| 228-204 | 0.302 | 0.056 |
| 204-171 | 0.420 | 0.091 |
| 171-148 | 0.432 | 0.110 |
| 148-122 | 0.716 | 0.216 |
| 122-103 | 0.660 | 0.239 |
| 103-83 | 0.087 | 0.480 |
| 83-68 | 1.115 | 0.605 |
| 68-57 | 0.903 | 0.586 |
| 57-49 | 0.746 | 0.565 |
| 49-43 | 0.589 | 0.514 |
| 43-38 | 0.464 | 0.461 |
| 38-34 | 0.648 | 0.728 |

TABLE III-continued

Relationship Between Pore Diameter, Pore Volume and Pore Area

| Pore Diameter Å | Pore Volume (mm³/g) | Pore Area (m²/g) |
|---|---|---|
| 34-30 | 0.087 | 0.110 |

A large percentage of the pores in the aluminium complex have sizes in the range of 34–125 Å. The examined fibre had a specific surface area of 5.5 m²/g. The total surface area of pores smaller than 125 Å is about 4.5 m²/g. A non-treated CTMP has so few pores in this range as to lie beneath the detection limit of the method used to determine the porosity.

The following examples are intended to illustrate the invention without restricting its scope.

EXAMPLE 1

A CTMP-pulp was impregnated with poly(iron sulphate) (Kemira) in a quantity such that the iron content was 2% by weight, for a period of 10 minutes. The pH was adjusted to 7 during the impregnating process.

Absorption rate and absorption capacity were measured in accordance with "The Porous Plate Testing Apparatus" (see Textile Res. J., pages 356–366, 1967, Burgeni and Kapur: "Capillary Sorption Equilibria in Fiber Mass"). The specific surface area was measured in accordance with the BET-method.

The following results were obtained:

|  | Absorption Rate (ml/s) | Absorption Capacity (ml/g) | Specific Surface Area m²/g |
|---|---|---|---|
| Reference | 2.61 | 9.46 | 1.06 |
| Sample | 3.82 | 9.44 | 2.52 |

EXAMPLE 2

A CTMP-pulp was impregnated with 2.3% by weight sodium metasilicate for 30 minutes. The pulp was dewatered and then impregnated with poly(aluminium chloride) (2% aluminium) for 30 minutes. The pH was adjusted to pH=9 during the impregnation process. The pulp was again dewatered after the impregnation process.

Absorption rate and specific surface area were measured in accordance with the methods mentioned in Example 1, and the following results were obtained:

| Aluminium (%) | Absorption rate (ml/s) | Specific Surface Area (m²/g) |
|---|---|---|
| 0 | 2.77 | 0.86 |
| 0.05 | 2.99 | 1.03 |
| 0.4 | 3.26 | 1.07 |
| 2 | 4.26 | 6.44 |

EXAMPLE 3

A CTMP-pulp was impregnated with sodium metasilicate (EKA)—chemical supplier, 2% by weight over a period of 30 minutes.

Absorption rate and specific surface area were measured in accordance with the methods mentioned in Example 1 and the following results were obtained:

|  | Absorption Rate (ml/s) | Specific Surface Area m²/g |
|---|---|---|
| Reference | 1.88 | 0.98 |
| Sample | 2.25 | 1.20 |

EXAMPLE 4

A CTMP-pulp was impregnated with 2% by weight sodium metasilicate for 10 minutes, whereafter the pulp was dewatered. The dewatered pulp was then impregnated with poly(aluminium chloride), containing 2% by weight aluminium, for a period of 10 minutes while adjusting the pH to 9. The pulp was then dewatered.

Absorption rate and specific area were measured in accordance with the methods mentioned in Example 1 and the following results were obtained.

|  | Absorption Rate (ml/s) | Specific Surface Area m²/g |
|---|---|---|
| Reference | 1.93 | 1.07 |
| Sample | 4.59 | 4.70 |

EXAMPLE 5

A CTMP pulp was impregnated with poly(aluminium chloride) (2% by weight aluminium) for 10 minutes. The pH of the pulp suspension was adjusted to pH 9. The pulp was dewatered after the impregnating process.

Absorption rate and specific surface area were measured in accordance with the methods mentioned in Example 1 and the following results were obtained:

|  | Absorption Rate (ml/s) | Specific Surface Area m²/g |
|---|---|---|
| Reference | 1.28 | 0.98 |
| Sample | 3.23 | 1.31 |

Subsequent to bleaching the pulp, the pulp was found to contain residual quantities of silicate.

EXAMPLE 6

$CaCO_3$ was added in an amount of 3% by weight Ca to an aqueous suspension of CTMP-fibres while adjusting the pH to 7. The pulp was treated in other respects in the manner described in the earlier examples, resulting in a satisfactory increase in the specific surface area and therewith a subsequent increase in the absorption rate.

EXAMPLE 7

Synthetic fibres consisting of polyester fibres (du Pont, "DACRON D 342 N5D") having a length of 6 mm were impregnated with an aluminium silicate complex. In one experiment, the fibres were impregnated solely with poly(aluminium chloride) (2% by weight aluminium) while in the other experiment the polyester fibres were first impregnated with sodium metasilicate (2% by weight) over a period of 10 minutes, whereafter the fibres were impregnated with poly(aluminium chloride) (2% by weight aluminium) while adjusting the pH to 9.

Absorption rate and specific surface area were measured in accordance with the methods recited in Example 1.

The following results were obtained:

|  | Sodium-metasilicate (% by weight) | Aluminium-conc (% by weight) | Absorp. Rate (ml/s) | Absorp. Cap. (ml/g) | Spec. Surf. Area (m²/g) |
|---|---|---|---|---|---|
| Ref. | 0 | 0 | 0.01 | 0.18 | 0.25 |
| Sample | 0 | 2 | 0.65 | 10.19 | 2.31 |
| Sample | 2 | 2 | 0.51 | 10.03 | 2.64 |

EXAMPLE 8

A dried, bleached CTMP-pulp was impregnated with a cationic polymer consisting of "DADMAC" from Dow Chemicals in an amount of 100 µeq/g. The impregnation time was about 30 minutes. Subsequent to impregnation, the pulp was dewatered and thereafter impregnated with 6% by weight sodium metasilicate while adjusting the pH to 9. The pulp was then dewatered and dried.

Absorption rate and specific surface area were measured in accordance with Example 1 above and the following results were obtained:

|  | Absorption Rate (ml/s) | Total Absorption (ml/g) | Specific Surface Area m²/g |
|---|---|---|---|
| Reference | 1.90 | 9.39 | 1.09 |
| Sample | 3.20 | 9.64 | 1.51 |

EXAMPLE 9

A non-dried, unbleached CTMP-pulp was impregnated with a cationic polymer consisting of "DADMAC" from Dow Chemicals, in an amount of 100 µeq/g. The impregnation time was about 30 minutes. Subsequent to impregnation, the pulp was dewatered and thereafter impregnated with 6% by weight sodium-metasilicate and the pH was adjusted to 9. The pulp was then dewatered and dried.

Absorption rate and specific surface area were measured in accordance with Example 1 above and the following results were obtained:

|  | Absorption Rate (ml/s) | Total Absorption (ml/g) | Specific Surface Area m²/g |
|---|---|---|---|
| Reference | 1.08 | 10.00 | 0.89 |
| Sample | 3.38 | 10.01 | 1.40 |

EXAMPLE 10

A non-dried, bleached CTMP-pulp was impregnated with a cationic polymer consisting of "DADMAC" from Dow Chemicals in a quantity of 100 µeq/g. The impregnation time was about 30 minutes. After impregnation, the pulp was dewatered and thereafter impregnated with 6% by weight sodium-metasilicate and the pH was adjusted to 9. The pulp was then dewatered and dried.

In a further experiment, the pulp was treated solely with sodiummetasilicate and in another experiment solely with cationic polymer.

Absorption rate and specific surface area were measured in accordance with Example 1 above and the following results were obtained:

|  | Sodium-metasilicate | Cationic Polymer | Absorption Rate (ml/s) | Specific Surface Area (m²/g) |
|---|---|---|---|---|
| Reference | – | – | 1.59 | 1.08 |
| Sample | + | – | 2.25 | 1.21 |
| Sample | – | + | 1.26 | 1.00 |
| Sample | + | + | 3.71 | 2.31 |

N.B.:
"–" = not present, "+" = present.

It is evident from Examples 1–10 above that an increase in the specific surface area and a subsequent increase in absorption rate is achieved with fibres of mutually different kinds intended for use primarily as fluff pulp for absorption purposes when the fibres are treated with hydrophilic chemicals, said chemicals being anchored to the surfaces of the fibres in the form of a porous layer.

It is particularly evident from Examples 8–10 that anchoring of the layer to the fibre surface can be improved by adding polymers, either synthetic or native polymers.

The inventive fibres have also been tested with respect to their function in sanitary products. Such products include an absorption body consisting of fluff pulp for the purpose of imparting to the product volume, shape stability and absorbency in combination with the ability to contain (store) a certain quantity of liquid. So-called superabsorbents can be added to improve liquid containment of the absorption body, the function of such superabsorbents being to store liquid and also to retain liquid under pressure.

One problem with the use of superabsorbents, however, is that high superabsorbent contents can result in blocking effects which impede dispersion of the liquid in the absorbent body. Present-day products of this nature normally include about 10–30% by weight superabsorbents.

Improved properties can be obtained, particularly higher absorption rates and improved liquid dispersion in the peripheral region of the product, when the superabsorbents are replaced, totally or partially, or supplemented with an inventive fibre.

The amount of aluminium-salt impregnated fibre according to the invention constitutes 10–100% calculated on the weight of the absorption material.

LIQUID SPREADING IN THE X, Y AND Z DIRECTIONS

A small experiment was carried out in which "Salsorb 84" (superabsorbent from Allied Colloids Ltd.) was admixed with pulp consisting of fibres according to the present invention. Sample bodies were produced in accordance with a method devised by Brill, J. W., "New Scandinavian Fluff Test Methods", Tappi Journal, Vol. 66, No. 11, 1983. In this case, 20% by weight superabsorbent was admixed with the pulp. The sample bodies were evaluated in an X. Y and Z direction absorption dispersion meter. The apparatus used was a dispersion meter produced by Holger Hollmark at STFI. Stockholm. (SCAN P 39 X, Holger Hollmark and Per-Olof Bethge, "Water Absorption Rate and Capacity"). Results and data are set forth in the following Table.

The fibre pulp according to the present invention disperses the liquid more rapidly in the aforesaid three directions than conventional CTMP, even with these high superabsorbent admixtures.

TABLE IV

Absorption Time Measured in a Dispersion Meter

| | Absorption time(s) | | |
|---|---|---|---|
| | X-direction | Y-direction | Z-direction |
| Reference (20% "Salsorb 84") | 7.17 | 8.41 | 5.37 |
| Sample | 5.85 | 5.99 | 3.46 |

Liquid dispersion in a horizontal direction is clearly improved.

The improved ability of the fibres to disperse liquid, both horizontally and vertically, remains even together with superabsorbents.

What is claimed is:

1. Fibres of organic material in the form of fluff, for use in absorption articles, wherein the fibres have firmly anchored on surfaces thereof by chemical bonding a porous hydrophilic layer having a thickness less than 2000 Å and containing as a main component positive inorganic ions, the specific surface area of the fibres being at least 1.2 m$^2$/g and the hydrophilic porous layer having a contact angle with water of at most 70°.

2. Fibres according to claim 1, wherein the fibres are selected from the group consisting of cellulosic fibres, synthetic fibres and natural fibres, and a mixture thereof.

3. Fibres according to claim 1, wherein said contact angle is at most 65°.

4. Fibres according to claim 1, wherein the hydrophilic porous layer consists of chemical compounds of negative ions and positive inorganic ions.

5. Fibres according to claim 4, wherein the positive ions are selected from the group consisting of alkali metal ions and alkaline earth metal ions, $Al^{3+}$, $Fe^{3+}$, $Fe^{2+}$, $Mn^{2+}$, $Cu^{2+}$ and $Mg^{2+}$ ions and a mixture thereof and the compounds of said ions consist of salts or hydroxides.

6. Fibres according to claim 4 wherein the alkali metal ions are supplied in the form of sodium metasilicate.

7. Fibres according to claim 4, wherein the alkaline earth metal ions are supplied in the form of calcium sulphate, calcium carbonate or calcium chloride.

8. Fibres according to claim 4, wherein the aluminium ions are supplied in the form of poly(aluminium chloride) or poly(aluminium sulphate) or aluminium phosphate or sodium aluminate.

9. Fibres according to claim 4, wherein the iron ions are supplied in the form of poly(iron sulphate) or poly(iron chloride).

10. Fibres according to claim 4, wherein the porous hydrophilic layer is anchored on the fibres in the presence of silicate.

11. Fibres of organic material in the form of fluff, for use in absorption articles, wherein the fibres have firmly anchored on surfaces thereof by chemical precipitation a porous hydrophilic layer having a thickness less than 2000 Å and containing as a main component positive inorganic ions, the specific surface area of the fibres being at least 1.2 m$^2$/g, and the hydrophilic porous layer having a contact angle with water of at most 70°.

12. A method of producing fibres of organic material, in the form of fluff, by treating the fibres with chemicals wherein positive inorganic ions are a main component in such a way as to apply to the fibre surfaces a porous hydrophilic layer that has a thickness less than 2000 Å and that includes said chemicals, said layer being firmly anchored to the fibre surfaces by chemical bonding, so that subsequent to treatment the specific surface area of the fibres is at least 1.2 m$^2$/g and the hydrophilic porous layer presents a contact angle with water of at most 70°.

13. A method according to claim 12, wherein the fibres are treated by bringing said fibres into contact with said chemicals by spraying the fibres with an aqueous solution of said chemicals.

14. A method according to claim 12, wherein the fibres are treated by bringing said fibres into contact with said chemicals by adding an aqueous suspension of said fibres with said chemicals.

15. A method according to any one of claim 12, further comprising drying the treated fibres.

16. A method according to claim 12, wherein the fibres are selected from the group consisting of cellulosic fibres, synthetic fibres, natural fibres, and a mixture thereof.

17. A method according to claim 12, wherein the hydrophilic porous layer presents a contact angle with water of at most 65°.

18. A method according to claim 12, wherein the chemicals consist of compounds of negative ions with positive inorganic ions.

19. A method according to claim 18, wherein the ions are selected from the group consisting of alkali metal ions and alkaline earth metal ions, $Al^{3+}$, $Fe^{3+}$, $Fe^{2+}$, $Mn^{2+}$, $Cu^{2+}$ and $Mg^{2+}$ ions and a mixture thereof and the compounds of said ions consist of salts or hydroxides.

20. A method according to claim 19, wherein the alkali metal ions are added in the form of sodium metasilicate.

21. A method according to claim 19, wherein the alkaline earth metal ions are supplied in the form of calcium sulphate, calcium carbonate or calcium chloride.

22. A method according to claim 19, wherein the aluminium ions are supplied in the form of poly(aluminium chloride) or poly(aluminium sulphate) or aluminium phosphate or sodium aluminate.

23. A method according to claim 19, wherein the iron ions are supplied in the form of poly(iron sulphate) or poly(iron chloride).

24. A method according to claim 12, wherein the treatment is carried out in the presence of silicate.

25. A method of producing fibres of organic material, in the form of fluff, by treating the fibres with chemicals wherein positive inorganic ions are a main component in such a way as to apply to the fibre surfaces a porous hydrophilic layer that has a thickness less than 2000 Å and that includes said chemicals, said layer being firmly anchored to the fibre surfaces by chemical precipitation, so that subsequent to treatment the specific surface area of the fibres is at least 1.2 m$^2$/g, and the hydrophilic porous layer presents a contact angle with water of at most 70°.

* * * * *